(12) United States Patent
Matsuhira

(10) Patent No.: US 7,927,440 B2
(45) Date of Patent: Apr. 19, 2011

(54) BONDING METHOD AND METHOD OF MANUFACTURING A DISPLAY DEVICE

(75) Inventor: Tsutomu Matsuhira, Chiba (JP)

(73) Assignee: Seiko Instruments Inc. (JP)

( * ) Notice: Subject to any disclaimer, the term of this patent is extended or adjusted under 35 U.S.C. 154(b) by 288 days.

(21) Appl. No.: 12/085,806

(22) PCT Filed: Nov. 28, 2006

(86) PCT No.: PCT/JP2006/323643
§ 371 (c)(1),
(2), (4) Date: Jul. 21, 2008

(87) PCT Pub. No.: WO2007/063818
PCT Pub. Date: Jun. 7, 2007

(65) Prior Publication Data
US 2009/0038734 A1    Feb. 12, 2009

(30) Foreign Application Priority Data

Nov. 30, 2005    (JP) ................................. 2005-346400

(51) Int. Cl.
*B32B 41/00* (2006.01)
(52) U.S. Cl. ...................... 156/64; 156/272.2; 156/275.5
(58) Field of Classification Search .................. 156/64, 156/272.2, 275.5, 295, 297, 299, 351, 378
See application file for complete search history.

(56) References Cited

U.S. PATENT DOCUMENTS
5,795,430 A  *  8/1998  Beeteson et al. ............. 156/350

FOREIGN PATENT DOCUMENTS

| JP | 61284648 | * | 12/1986 |
| JP | 06082778 | * | 3/1994 |
| JP | 08261953 | * | 10/1996 |
| JP | 10339705 | * | 12/1998 |
| JP | 11287937 | * | 10/1999 |
| JP | 2002139455 | * | 5/2002 |
| JP | 2004325788 | * | 11/2004 |

OTHER PUBLICATIONS

JP 2002-139455—Machine Translation. May 2002.*
JPO Communication in Japanese Counterpart Application No. 2007-547933.
Patent Abstracts of Japan, publication No. JP6082778, publication date Mar. 25, 1994.
Patent Abstracts of Japan, publication No. JP11287937, publication date Oct. 19, 1999.
Patent Abstracts of Japan, publication No. JP2002139455, publication date May 17, 2002.
Patent Abstracts of Japan, publication No. JP2004325788, publication date Nov. 18, 2004.
Patent Abstracts of Japan, publication No. 2002-139455, publication date May 17, 2002.

* cited by examiner

*Primary Examiner* — George R Koch, III
(74) *Attorney, Agent, or Firm* — Adam & Wilks

(57) ABSTRACT

Air bubbles or foreign objects in a transparent adhesive layer that bonds a transparent plate and a plate-like member together in full-surface contact are detected without fail. For the detection, an optical fiber or the like is used to irradiate the adhesive layer with light from a side, the cast light is guided through the adhesive layer, and a state of the adhesive layer is checked with the guided light. A check that discriminates defects in the adhesive layer from defects in the bonded transparent plate is thus made possible.

8 Claims, 1 Drawing Sheet

BONDING METHOD AND METHOD OF MANUFACTURING A DISPLAY DEVICE

CROSS-REFERENCE TO RELATED APPLICATION

This application is a U.S. national stage application of International Application No. PCT/JP2006/323643, filed Nov. 28, 2006, claiming a priority date of Nov. 30, 2005, and published in a non-English language.

BACKGROUND OF THE INVENTION

1. Field of the Invention

The present invention relates to a method of bonding a transparent substrate and a substrate together with a liquid adhesive in a manner that brings the two into full-surface contact with each other. For example, the present invention relates to bonding a transparent cover plate of a cellular phone or other similar devices to a flat display such as a liquid crystal display device, a plasma display, an organic EL display, an inorganic EL display, or an FED, or bonding a touch panel to a flat display.

2. Description of the Related Art

Conventionally, a general method to place a transparent touch panel on a display device has been to fix the transparent touch panel to the perimeter of the display device by providing cushion rubber with adhesive about 0.5 mm or more in thickness. Another method is to bond the liquid crystal display device and the touch panel together in full-surface contact with the use of a transparent adhesive (see, for example, JP 09-274536 A, which is hereinafter referred to as Patent Document 1).

Still another known method uses a transparent adhesive sheet to bond the touch panel and the display panel together (see, for example, JP 2004-5540 A, which is hereinafter referred to as Patent Document 2). An advantage of full-surface contact bonding with the use of the transparent adhesive sheet is that the adhesion of one side surface of the transparent adhesive sheet can be adjusted such that, if air bubbles, foreign objects, and the like are caught in-between during bonding, the sheet is peeled off and stuck again after cleaning. In cellular phones, a transparent cover plate is placed over a liquid crystal display device, and a black-colored member or the like is formed by printing in the perimeter of the transparent cover plate outside a display area of the liquid crystal display. Commonly, an elastic member made of rubber or the like is interposed between the printed member and the liquid crystal display outside the display area.

Another way to bond the display area in a full-surface contact manner is a sheet obtained by laminating a silicon gel layer and a silicone rubber layer (see, for example, JP 2004-101636, which is hereinafter referred to as Patent Document 3).

Recently, demand has been growing for thinner cellular phones which measure 0.1 mm or less between the transparent cover plate and the liquid crystal display. Employed for the transparent cover plate is transparent plastic such as an acrylic or polycarbonate, glass, or the like. The transparent cover plate includes a low reflective film made up of layers of materials to vary the refractive index in stages, an electromagnetic shield formed of copper, aluminum, or the like and forming a grid-like etching pattern, and a hard coat for preventing scratches. In the case of a glass cover plate, a film sheet for preventing cracking, a film sheet subjected to anti-glare treatment to prevent specular reflection, or the like is stuck over the glass surface. The transparent cover plate and the flat display have a rectangular shape in most cases. Variations of the touch panel include resistive panels (analog resistive film type and digital resistive film type), capacitive (CAP) panels, and surface acoustic wave (SAW) panels.

Air bubbles and foreign objects trapped during bonding are a serious issue common to all of various methods of bonding a liquid crystal display to a touch panel or a transparent cover plate that have been proposed. Although whether air bubbles and foreign objects are being trapped is checked by casting light from the screen side of the transparent cover plate or of the touch panel after bonding in the case of a transparent adhesive sheet, or before curing in the case of a transparent adhesive, there are following problems. The check may detect a foreign object but cannot tell whether the foreign object is in the bonded touch panel or transparent cover plate or in the bonded adhesive layer. It is very difficult to confirm the location of a defect in the touch panel or the transparent cover plate before conducting the post-bonding check. Also, in the case of a photo-curing transparent adhesive, especially a visible-light curable adhesive, the light cast for the check accelerates the curing of the adhesive to a point that makes it difficult to peel when a defect is found, unless the check is finished quickly.

SUMMARY OF THE INVENTION

The present invention has been made in view of the above-mentioned problems, and therefore has an object to provide a method that checks for foreign objects, air bubbles and other defects in the adhesive layer alone by discriminating them from defects in the transparent cover plate or the touch panel and, in the case of a photo-curing transparent adhesive is employed for bonding, that prevents a curing reaction to the check in the adhesive.

According to the present invention, a method of bonding a transparent member to a plate-like member includes a first step of forming a transparent adhesive layer between the transparent member and the plate-like member; and a visual check step of casting light from a side of the transparent adhesive layer to check the transparent adhesive layer and its interface. A visual check for anomalies in the adhesive sheet and its interface alone is thus made possible by guiding the cast light so as to travel only in the adhesive layer and illuminate defects such as air bubbles and foreign objects in the adhesive layer.

In the above-mentioned method of the present invention, the transparent adhesive layer is a transparent adhesive sheet, and the first step includes the steps of attaching the transparent adhesive sheet to one of the transparent member and the plate-like member, and bonding the plate-like member and the transparent member together with the transparent adhesive sheet in full-surface contact.

When a photo-curing transparent adhesive is employed as the transparent adhesive layer, the first step is a step of filling a gap between the transparent member and the plate-like member with the transparent adhesive, and a state of the transparent adhesive is checked in the visual check step by casting light having a wavelength that does not cause a curing reaction in the transparent adhesive from a side of the transparent adhesive, and the method further includes the step of curing the transparent adhesive by casting light having a wavelength that causes a curing reaction in the transparent adhesive from the transparent member side. Also, when a photo-curing transparent adhesive is employed as the transparent adhesive layer, the first step is a step of filling a gap between the transparent member and the plate-like member with the transparent adhesive, and a state of the transparent adhesive is checked in the visual check step by casting light containing a wavelength that causes a curing reaction in the transparent adhesive, for a period of time short enough to prevent starting the curing, from a side of the transparent adhesive, and the method further includes the step of curing the transparent adhesive by casting light having a wavelength that causes a curing reaction in the transparent adhesive from the transparent member side. According to those methods where the adhesive is not cured in the visual check step, if it is judged in this step that the adhesive contains air bubbles or foreign objects, the adhesive can be readily removed for re-bonding, and the transparent member and the plate-like member do not have to be discarded. If the item being checked is judged in this step as non-defective, on the other hand, the item can be irradiated with light under a condition that causes a curing reaction in the adhesive.

A method of manufacturing a display device of the present invention in which a transparent plate and a display element are bonded together includes a step of forming a transparent adhesive layer between the transparent plate and the display element, and an visual check step of checking a state of the transparent adhesive layer by casting light from a side of the transparent adhesive layer.

In this case, light is cast in the visual check step under a condition that does not cause a curing reaction in the transparent adhesive layer, and the method further includes, after the visual check step, an adhesive curing step of casting light from the transparent plate side under a condition that causes a curing reaction in the transparent adhesive layer. To elaborate, in the visual check step, light having a wavelength that does not start a curing reaction is cast, or light containing a wavelength that causes a curing reaction is cast for a period of time short enough to prevent starting a curing reaction, and the visual check step may be followed by a step of casting light containing a wavelength that accelerates a curing reaction.

Such methods make it possible to check for air bubbles, foreign objects, and the like in the transparent adhesive with the use of light cast from a side of the transparent adhesive and having a wavelength that does not start a curing reaction and, for a defective item, to immediately repair the item that is being checked if an anomaly is found (by removing the transparent adhesive and applying a new coat of the transparent adhesive to fill the gap between the transparent plate and the plate-like member) before conducting an visual check again and, for a non-defective item, to irradiate the photo-curing adhesive with light of a wavelength that causes a curing reaction, thereby bonding the transparent plate and the plate-like member together.

DETAILED DESCRIPTION OF THE INVENTION

Figure 1:
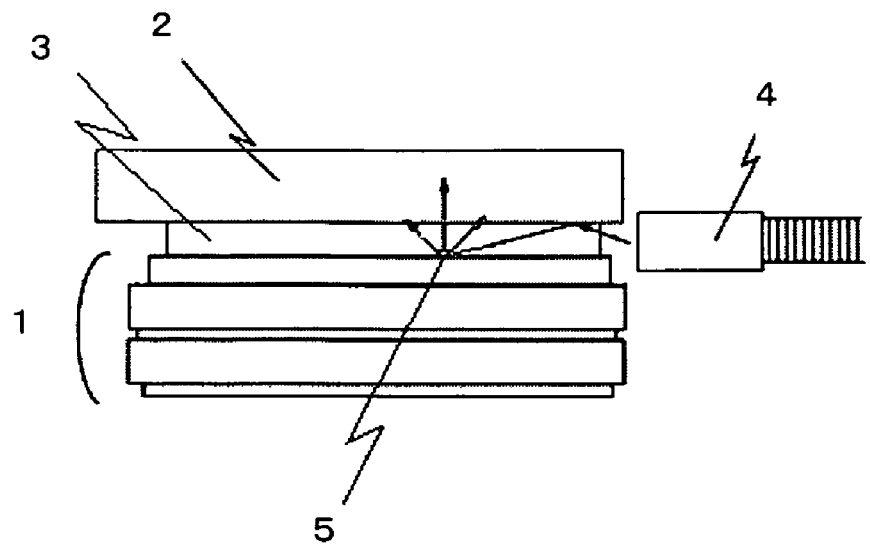
FIG. 1 is a schematic side view illustrating how a check is conducted according to Embodiment 1 of the present invention.

A bonding method according to the present invention is as follows. A transparent adhesive sheet is attached to a transparent cover plate or a touch panel. Thereafter, the transparent adhesive sheet is bonded to a flat display. After the bonding, the transparent adhesive sheet or a transparent adhesive layer is irradiated with light from a side through an optical fiber. The transparent adhesive sheet is irradiated along the entire length of one side in order to check for air bubbles and foreign objects. If the transparent adhesive sheet contains air bubbles, the light is scattered and the defective portions appear as bright spots. When a defect is found, the transparent cover plate or the touch panel is peeled to clean the adhesive off, bonded again, and re-checked. The peeling is not particularly difficult since the adhesive is not cured yet. To elaborate, when a transparent plate such as the transparent cover plate or the touch panel and the flat display are bonded together with the transparent adhesive sheet, an item judged as defective in an visual check is repaired by peeling the transparent plate and the flat display off each other and removing the transparent adhesive sheet while the adhesive is uncured, and then bonding them again in the same way.

According to the present invention, a method of bonding the transparent plate such as the transparent cover plate or the touch panel and the flat display together with a photo-curing transparent adhesive is as follows. The transparent adhesive is applied to the transparent plate, which is then flipped upside down. The transparent adhesive and the flat display are brought into contact slowly so that air bubbles are not trapped, and a gap between the transparent plate and the flat display is filled with the transparent adhesive. After the filling, an adhesive layer is irradiated with light from a side. The light cast to the adhesive layer is emitted through an optical fiber from a yellow light source which mixes green light and red light, since the wavelength at which a photoinitiator reacts is 420 nm in the case of a visible-light curable transparent adhesive. The adhesive layer is irradiated along the entire length of one side in order to check for air bubbles and foreign objects. If the adhesive layer contains air bubbles, the light is scattered and the defective portions appear as bright spots. Similarly, if a metal piece is contained, it scatters the light and creates a bright spot. Lint, too, appears outlined by light, but the light is weaker than that of air bubbles. When any such defect is found, the transparent plate is peeled from the flat display, and the transparent adhesive filling the gap is cleaned by wiping it off with a clean waste cloth or the like. Thereafter, the transparent adhesive is applied again to bond the transparent plate and the flat display together, which is then checked for defects. A non-defective item is irradiated with light in order to cure the transparent adhesive. The check has to be finished within five seconds in the case where the employed transparent adhesive is of visible-light curable type and the check uses white light. An item judged in the visual check as defective is repaired by peeling the transparent plate and the flat display off each other and removing the transparent adhesive while the transparent adhesive is in a liquid state, and then bonding them together again in the same way.

A display device manufacturing method in which a transparent plate and a display element are bonded together according to the present invention includes a step of forming a transparent adhesive layer between the transparent plate and the display element, and an visual check step for checking a state of the transparent adhesive layer by casting light from a side of the transparent adhesive layer.

The light cast from the side of the transparent adhesive layer is light having a wavelength that does not start a curing reaction in the transparent adhesive layer. The visual check step may be followed by an adhesive curing step for casting light having a wavelength that causes a curing reaction in the transparent adhesive from the transparent plate side.

Alternatively, the light cast from the side of the transparent adhesive layer may be light containing a wavelength that does not start a curing reaction in the transparent adhesive, and cast for a period of time short enough to prevent the transparent adhesive from starting curing, and the visual check step may be followed by an adhesive curing step for casting light having a wavelength that causes a curing reaction in the transparent adhesive from the transparent plate side.

Examples of the material of the transparent plate include plastic and glass, and the transparent plate may be a touch panel or a covering member.

Embodiment 1

An embodiment of the present invention is described below with reference to one of the accompanying drawings. FIG. 1 is a side view showing a visual check step of a bonding method according to this embodiment. A liquid crystal display 1 and a transparent member in the form of a cover plate 2 are bonded together with a transparent adhesive sheet 3. The liquid crystal display 1 is a TFT liquid crystal display. TFT elements are formed on one of two transparent substrates each of which is made of glass and has a thickness of 0.3 mm. Formed on the other opposite transparent substrate is a color filter. Between those two transparent substrates, a TN liquid crystal is oriented along orientation films, which are formed on surfaces of the transparent substrates. A polarizing plate is attached to each transparent substrate. The transparent cover plate 2 is an acrylic plate with a thickness of 1.5 mm. A side of the transparent cover plate 2 opposite to the displaying side is painted black in an area that overlies or falls on the perimeter of screen of the display. The transparent adhesive sheet 3 is acrylic-based and has a thickness of 150 µm. The adhesion of the transparent adhesive sheet 3 is strong on the transparent cover plate side and weak on the liquid crystal display side. Air bubbles 5 are trapped in an interface between the transparent adhesive sheet 3 and the liquid crystal display 1. Light is cast from a check-use optical fiber 4, guided through the transparent adhesive sheet 3, scattered by the air bubbles 5, and appears as bright spots when viewed from the displaying direction. The air bubbles 5 are thus detected. The transparent cover plate 2 and the transparent adhesive sheet 3 are peeled from the liquid crystal display 1 to clean a portion of the liquid crystal display 1 where the air bubbles have been located. The transparent cover plate 2 and the liquid crystal display 1 are then bonded together once more with the transparent adhesive sheet 3, and run through a check with the use of the optical fiber 4. If the check confirms that there are no defects, the bonding is completed.

This embodiment employs a liquid crystal display but may instead employ an organic EL display, an FED, an SED, a plasma display, or an STN or LTPS liquid crystal display. Also, the transparent cover plate bonded to the display is not limited to an acrylic-based plastic plate, but may be made of other types of transparent resin or glass such as hard glass, non-alkali glass, or soda glass. The transparent cover plate may be replaced with a resistive film analog touch panel, a surface acoustic wave (SAW) touch panel, or a capacitive (CAP) touch panel. The transparent adhesive sheet is not limited to an acrylic-based sheet, but may be a silicon-based sheet, a laminate sheet of a silicon gel sheet and a silicone rubber sheet, or a laminate or single-layer sheet of other materials. Light used for the check does not have to be cast from an optical fiber, and other measures can be employed as long as the transparent adhesive layer is irradiated with light.

Embodiment 2

Figure 2:
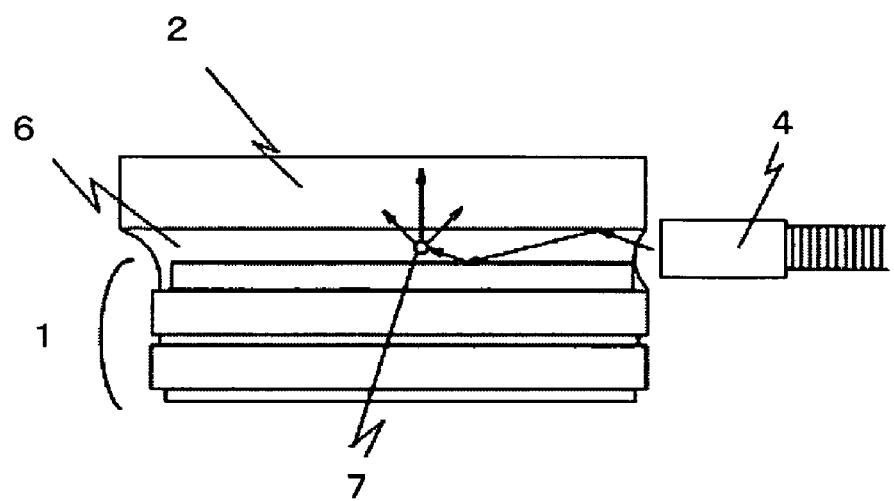
FIG. 2 is a schematic side view illustrating how a check is conducted according to Embodiment 2 of the present invention.

An embodiment of the present invention is described below with reference to one of the accompanying drawings. FIG. 2 is a side view showing a visual check step of a bonding method according to this embodiment. Between a liquid crystal display 1 and a transparent member or cover plate 2, a transparent adhesive 6 which is not cured yet is filled. The liquid crystal display 1 is a TFT liquid crystal display. TFT elements are formed on one of two transparent substrates each of which is made of glass and has a thickness of 0.3 mm. Formed on the other opposite transparent substrate is a color filter. Between those two transparent substrates, a TN liquid crystal is oriented along orientation films, which are formed on the surfaces of the transparent substrates. A polarizing plate is attached to each transparent substrate. The transparent cover plate 2 is an acrylic plate with a thickness of 1.5 mm. A side of the transparent cover plate 2 opposite to the displaying side is painted black in an area that falls on or overlies the perimeter of screen of the display.

The transparent adhesive 6 has a thickness of about 50 µm, and is a visible-light curable adhesive, and its photoinitiator starts a curing reaction at a wavelength of 420 nm, which means that, when irradiated with light having a wavelength of 420 nm, the transparent adhesive 6 begins to cure. Accordingly, yellow light created by mixing green light and red light is used in the check. The check can employ any light as long as the light's wavelength is not around 420 nm, and green light or red light may be used, provided that it does not affect the detection ratio of the check. An item may be checked twice by light of the same color or of two different colors. It is also possible to check an item multiple times by light of multiple colors.

The yellow light cast from a check-use optical fiber is guided through the adhesive layer and illuminates air bubbles 7 trapped in the transparent adhesive 6, thereby causing the air bubbles 7 to appear as bright spots detected by the human eye from the screen direction. The detection is not particularly limited to one by the human eye but may be made through image processing by a CCD camera. The entire bonding surface can be checked by casting light such that the optical fiber scans along a check direction side. The optical fiber does not have to be a spot irradiation type, and fibers may be arranged in a line for the check. When air bubbles, foreign objects, or other defects are detected in the adhesive layer, the liquid crystal display 1 and the transparent cover plate 2 are peeled from each other and the adhesive 6 filling the gap between the two is wiped off. The gap is then refilled with the adhesive and the check is conducted. If the check confirms that there are no defects, light in a range around 420 nm is cast from the transparent cover plate direction and from a side thereof, thus curing the adhesive 6 and completing the display.

The photo-curing transparent adhesive 6 is not limited to a visible-light curable type, but may be an ultraviolet-curable type. In this case, visible light can be employed in the check. In the case where the transparent adhesive 6 is a visible-light curable adhesive, curing does not start if irradiation with visible light is for a short period of time, approximately, five seconds. Irradiation longer than five seconds will start the curing reaction, although it depends on the intensity of illumination. How the transparent cover plate 2 and the liquid crystal display 1 are bonded is not particularly limited, but methods that can prevent accidental trapping of air bubbles and foreign objects as much as possible are preferred.

This embodiment employs a liquid crystal display by way of an example, but may instead employ an organic EL display, an FED, an SED, a plasma display, or an STN or LTPS liquid crystal display. Also, the transparent cover plate bonded to the display is not limited to an acrylic-based plastic plate, but may be made of other types of transparent resin or glass such as hard glass, non-alkali glass, or soda glass. The transparent cover plate may be replaced with a resistive film analog touch panel, a surface acoustic wave (SAW) touch panel, or a capacitive (CAP) touch panel. Light used for the check does not have to be cast from an optical fiber, and other measures can be employed as long as the transparent adhesive layer is irradiated with light.

The above-mentioned bonding methods ensure that air bubbles or foreign objects trapped in the transparent adhesive or the transparent adhesive sheet are detected through a check, which means that re-bonding can be executed by standards of defects caused by bonding, such as air bubbles and foreign objects. Accordingly, defects in the adhesive can be distinguished from defects in the touch panel or the transparent cover plate, unnecessary re-bonding is eliminated, and the display production is stabilized. Also, in the case where a photo-curing transparent adhesive is employed, a reliable check that does not accelerate the curing of the adhesive is made possible.

The invention claimed is:

1. A method of manufacturing a display device in which a transparent member and a polarizing plate attached on a surface of a display element are bonded together, comprising:
   a first step of filling a gap between the transparent member and the polarizing plate with a liquid, photo-curing, transparent adhesive;
   a light irradiation step of casting light from a side of the photo-curing transparent adhesive to guide the light through a layer of the photo-curing transparent adhesive;
   a visual check step of checking for the presence of foreign objects and air bubbles in an interior and at an interface of the layer using the light guided through the layer while the photo-curing transparent adhesive is not cured; and
   a step of curing the photo-curing transparent adhesive by casting light having a wavelength that causes a curing reaction in the photo-curing transparent adhesive from a side of the transparent adhesive layer.

2. A method of manufacturing a display device in which a transparent member and a polarizing plate attached on a surface of a display element are bonded together according to claim 1; wherein the photo-curing transparent adhesive is further cured by casting the light having a wavelength that causes a curing reaction in the photo-curing transparent adhesive from a side of the transparent member.

3. A method of manufacturing a display device in which a transparent member and a polarizing plate attached on a surface of a display element are bonded together according to claim 2; wherein the transparent member opposite to the displaying side is painted black in an area that overlies the perimeter of screen of the display.

4. A method of manufacturing a display device in which a transparent member and a polarizing plate attached on a surface of a display element are bonded together according to claim 1; wherein the light cast from the side of the photo-curing transparent adhesive in the light irradiation step has a wavelength that does not cause a curing reaction in the photo-curing transparent adhesive.

5. A method of manufacturing a display device in which a transparent member and a polarizing plate attached on a surface of a display element are bonded together to claim 4;
   wherein the photo-curing transparent adhesive is a visible-light curable adhesive, and the light cast from the side of the photo-curing transparent adhesive in the light irradiation step is red light, green light, or yellow light obtained by mixing red light and green light.

6. A method of manufacturing a display device in which a transparent member and a polarizing plate attached on a surface of a display element are bonded together according to claim 4; wherein the photo-curing transparent adhesive is a visible-light curable adhesive, and the light cast from the side of the photo-curing transparent adhesive in the light irradiation step is a light of multiple colors that does not include light having a wavelength of around 420 nm.

7. A method of manufacturing a display device in which a transparent member and a polarizing plate attached on a surface of a display element are bonded together according to claim 1; wherein the light cast from the side of the photo-curing transparent adhesive in the light irradiation step is light having a wavelength that causes a curing reaction in the photo-curing transparent adhesive, and the light is cast from the side the photo-curing transparent adhesive for five seconds or less.

8. A method of manufacturing a display device in which a transparent member and a polarizing plate attached on a surface of a display element are bonded together according to claim 1; wherein the light cast from the side of the photo-curing transparent adhesive in the light irradiation step radiates along a check direction side.

* * * * *